United States Patent

Dahlgran

[11] Patent Number: 5,939,324
[45] Date of Patent: Aug. 17, 1999

[54] PERFORMANCE EVALUATION SOIL SAMPLES UTILIZING ENCAPSULATION TECHNOLOGY

[75] Inventor: James R. Dahlgran, Idaho Falls, Id.

[73] Assignee: The United States of America as represented by the United States Department of Energy, Washington, D.C.

[21] Appl. No.: 08/982,894

[22] Filed: Dec. 2, 1997

[51] Int. Cl.⁶ ............................. G01N 1/38; G01N 1/28; G01N 33/24
[52] U.S. Cl. ................... 436/8; 73/863; 436/174
[58] Field of Search ............... 436/8, 174, 176; 73/863, 866.4, 1.01, 1.04

[56] References Cited

U.S. PATENT DOCUMENTS

| | | | |
|---|---|---|---|
| 3,516,846 | 6/1970 | Matson | 503/215 |
| 3,539,465 | 11/1970 | Hiestand et al. | 428/402.2 |
| 3,576,613 | 4/1971 | Fleming | 71/28 |
| 4,140,516 | 2/1979 | Scher | 504/220 |
| 4,166,720 | 9/1979 | Weber | 73/866 X |
| 4,683,209 | 7/1987 | Ismail et al. | 436/8 X |
| 4,931,362 | 6/1990 | Zsifkovits | 428/402.22 |
| 5,104,442 | 4/1992 | Schütze et al. | 504/281 |
| 5,432,089 | 7/1995 | Ryan et al. | 436/8 X |
| 5,461,027 | 10/1995 | Bergman | 504/347 |
| 5,526,705 | 6/1996 | Skotnikov et al. | 73/863 |
| 5,634,983 | 6/1997 | Kammerand | 134/25.1 |

FOREIGN PATENT DOCUMENTS

| 43381 | 4/1981 | Japan | 436/8 |
|---|---|---|---|
| 142271 | 6/1987 | Japan | 436/8 |

OTHER PUBLICATIONS

JP 407035661A copyright 1995, JPO month not given abstract of 7–35661 dated Feb. 7, 1995 Iizuka "Method for Preparing Soil Sample".

*Primary Examiner*—Thomas P. Noland
*Attorney, Agent, or Firm*—Daniel D. Park; Robert J. Fisher; William R. Moser

[57] ABSTRACT

Performance evaluation soil samples and method of their preparation using encapsulation technology to encapsulate analytes which are introduced into a soil matrix for analysis and evaluation by analytical laboratories. Target analytes are mixed in an appropriate solvent at predetermined concentrations. The mixture is emulsified in a solution of polymeric film forming material. The emulsified solution is polymerized to form microcapsules. The microcapsules are recovered, quantitated and introduced into a soil matrix in a predetermined ratio to form soil samples with the desired analyte concentration.

13 Claims, 1 Drawing Sheet

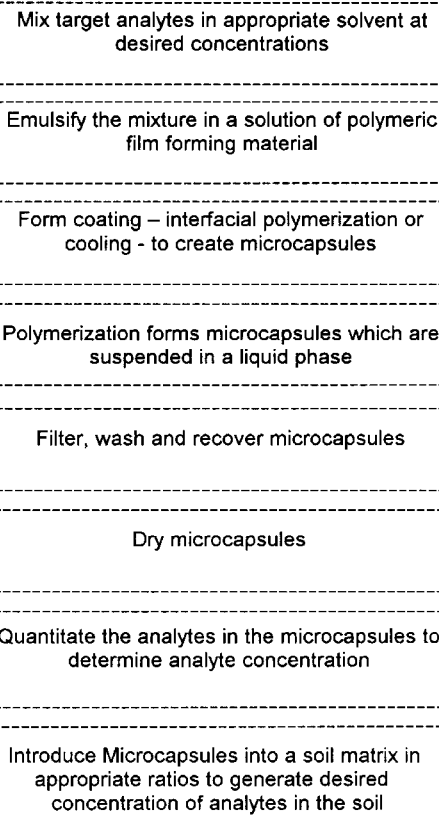

```
┌─────────────────────────────────────────────────┐
│  Mix target analytes in appropriate solvent at  │
│            desired concentrations               │
└─────────────────────────────────────────────────┘

┌─────────────────────────────────────────────────┐
│ Emulsify the mixture in a solution of polymeric │
│             film forming material               │
└─────────────────────────────────────────────────┘

┌─────────────────────────────────────────────────┐
│  Form coating – interfacial polymerization or   │
│       cooling - to create microcapsules         │
└─────────────────────────────────────────────────┘

┌─────────────────────────────────────────────────┐
│ Polymerization forms microcapsules which are    │
│          suspended in a liquid phase            │
└─────────────────────────────────────────────────┘

┌─────────────────────────────────────────────────┐
│       Filter, wash and recover microcapsules    │
└─────────────────────────────────────────────────┘

┌─────────────────────────────────────────────────┐
│                 Dry microcapsules               │
└─────────────────────────────────────────────────┘

┌─────────────────────────────────────────────────┐
│ Quantitate the analytes in the microcapsules to │
│        determine analyte concentration          │
└─────────────────────────────────────────────────┘

┌─────────────────────────────────────────────────┐
│  Introduce Microcapsules into a soil matrix in  │
│     appropriate ratios to generate desired      │
│       concentration of analytes in the soil     │
└─────────────────────────────────────────────────┘
```

FIG. 1

PERFORMANCE EVALUATION SOIL SAMPLES UTILIZING ENCAPSULATION TECHNOLOGY

CONTRACTUAL ORIGIN OF THE INVENTION

The United States Government has rights in this invention pursuant to employee/employer relationship of the inventor to the United States Department of Energy at the Radiological and Environmental Sciences Laboratory, Idaho Falls, Id.

BACKGROUND OF THE INVENTION

The present invention relates to performance evaluation soil samples and method of their manufacture, and, more particularly, to soil sample preparation using encapsulation technology to encapsulate analytes which are then introduced into a soil matrix for analysis and evaluation by analytical laboratories.

The demand for precise performance evaluation samples containing contaminants, including volatile organic compounds, in soil matrixes has increased greatly in the recent years. However, there is a lack of sample preparation technology which can accurately and easily replicate such contaminated soil matrices. Current technology for the preparation of performance evaluation soil samples containing volatile compounds has been to utilize solvent spiking (U.S. EPA and Private Sector performance evaluation program providers) or vapor fortification methodologies (J. Hewitt, U.S. Army Cold Regions Research and Engineering Laboratory). The common practice by U.S. EPA, as well as Private Sector companies, is to provide the analyst with a dilute solution of the compounds, or analytes, in methanol. The methanolic solutions can then be introduced either directly to the analytical technique (purge and trap or headspace analyses) or placed onto sand (which is used to simulate soil) just prior to instrumental analysis. However, this practice fails to simulate recovery of the analytes of interest from the soil due to lack of prolonged contact with the soil matrix and may even provide the analyst with an opportunity to analyze the spiking solution directly to assure accurate analytical results.

Furthermore, the vapor fortification method, as described above, yields soil samples with target analyte concentrations only in the low (<100) part-per-billion concentrations. These methods cannot be easily customized to increase concentrations and is not amenable to water soluble analytes. The vapor fortification method will only allow soil samples to reach a concentration that will be in equilibrium with the analyte vapors. Water-soluble analytes are not typically as volatile as non-water soluble analytes and thus come to equilibrium at much lower concentrations in the soil. Some of the concentrations for the water-soluble analytes in the final soil matrix may be significantly lower than ideal. Also, volatile target analytes are easily lost through handling or varying absorbtivity of the soil matrix.

To reduce some of the problems detailed above, the target analytes, including volatile analytes, need to be "hidden" from the analyst, provided to the analyst in the soil matrix, protected from the soil environment (biological activity) and provided in a wide range of concentrations which will result in accurate reproducible results.

In view of the foregoing, the general object of this invention is to provide performance evaluation soil samples which would mimic real world soil samples and provide consistent and realistic levels of contaminants within a soil matrix.

Another object of this invention is to provide a method of preparing soil samples using microencapsulation technologies to encapsulate and place contaminants within a soil matrix.

Yet another object of this invention is to provide soil samples containing microencapsulated volatile organic compounds which would facilitate the evaluation of a laboratory's analytical procedure.

Additional objects, advantages and novel features of the invention will become apparent to those skilled in the art upon examination of the following and by practice of the invention.

SUMMARY OF THE INVENTION

To achieve the foregoing and other objects, this invention provides performance evaluation soil samples and method of their preparation using encapsulation technology to encapsulate analytes which are introduced into a soil matrix for analysis and evaluation by analytical laboratories. Target analytes, such as volatile organic compounds, are mixed in an appropriate solvent at predetermined concentrations. The mixture is then emulsified in a solution of polymeric film forming material. The emulsified solution is polymerized to form microcapsules which become suspended in a liquid phase. The microcapsules are recovered by filtering and washing and are dried. The microcapsules are quantitated to determine the analyte concentration in the microcapsules. Finally, the microcapsules are introduced into a soil matrix in a predetermined ratio to form soil samples with the desired analyte concentration.

BRIEF DESCRIPTION OF THE DRAWINGS

FIG. 1 is a flow diagram of the soil sample preparation process using encapsulation technology to encapsulate target analytes which are placed into a soil matrix.

DESCRIPTION OF THE PREFERRED EMBODIMENT

The use of encapsulation technology, especially in the pharmaceutical field, is well known in the art, and there have been numerous patents and publications which have issued in this area. One method of encapsulation is the coacervation technique, which is the process by which a core material, or analyte, is emulsified in a solution of polymeric film forming material. Reducing the temperature of the emulsion, or otherwise controlling the emulsion, results in the formation of a film around the core material. Further process of the film forming solution results in a thickening of the film. The particle size formed from this procedure varies by emulsification technique and can range from 10–5000 A.

In the above method, the choice of the film forming component is critical to the utilization of the proposed final product. For the purpose of encapsulating volatile organics for later inclusion into soil performance evaluation samples the film must be either water soluble and/or methanol soluble due to the analytical methodology later applied, but relatively impermeable to the organics it encapsulates.

Another well known encapsulation technique is interfacial polymerization. In this technique, a monomer is dissolved in the solvent containing a target analyte. The solvent is then dispersed in a rapidly stirred solution containing a second monomer. Polymerization occurs at the interface between the two monomers to encapsulate the analytes of interest.

The above described, as well as other encapsulation techniques, can be used to prepare performance evaluation soil samples which can validate laboratory analytical methods and other assessment methodologies. In the preferred embodiment, the contaminants or target analytes chosen for encapsulation are volatile organic compounds. However, the invention is not limited to such and can include numerous other analytes of interest currently found in the performance evaluation market place. Such analytes can include oils and greases, nutrients, inorganic metals, organic compounds, cations and anions, and radiochemical compounds.

As shown in FIG. 1, a target analyte is prepared and placed into a solvent in the desired concentrations before encapsulation is performed. The solvent can be water, water with acid, or other such liquid that will act as a carrier for the target analyte. For instance, we may wish to encapsulate a buffered aqueous solution of radionuclides. The 'solvent' in this case would be a buffer solution made from water and a buffering agent.

In addition, the target analyte can be encapsulated as a pure component without the use of any solvents. This procedure is of particular advantage when it is desirable to reach higher concentrations or the analytes of interest require no dilution or solvent carrier. For example, when gasoline is encapsulated to simulate a soil sample contaminated with gasoline, a solvent is not needed to dilute or disperse the target analyte (gasoline).

In the preferred embodiment, the solvent into which the target analyte is spiked is iso-octane. However, the solvent could be any number of water immiscible substances. Closely controlling the amount of target analytes spiked into the iso-octane will result in a performance evaluation product with known concentrations. Knowing the percent loading, the amount of the target analyte added and the expected dilution of the final product with the soil matrix will result in a performance evaluation sample with a known concentrations of the target analyte, or at least a sample with the analyte in a very narrowly defined concentration range.

As described earlier, the encapsulation of the target analyte can be done by a variety of methods and techniques. The method should be chosen based on the target analyte to be encapsulated, the soil matrix in which the target analyte is to be added, and other such considerations for producing accurate and reproducible soil samples. In the preferred embodiment, interfacial polymerization of the spiked solvent produces coated particles, or microcapsules, which become suspended in a mobile phase. The phase is then filtered and washed to recover the microcapsules. Typically, the microcapsules are dried in the presence of some soil to prevent particle agglomeration. After recovery, the microcapsules are analytically quantitated to determine analyte concentrations. Finally, the microcapsules are then combined with a soil matrix in the desired amounts to create the final Performance Evaluation soil sample.

The soil matrix used for the creation of the performance evaluation soil samples can be derived from any source. Preferably, the soil matrix has an organic content less than 8% and has been dried and sieved to a uniform mesh size. The preferable mesh size is 60–80 mesh, however, 200 mesh will also work well.

In one sample trial, small amounts of pure solvents (BTEX: benzene, toluene, ethyl benzene and p-xylene) were encapsulated to examine lot to lot variability, particle size, homogeneity and coacervation issues. Analysis of these samples indicated the encapsulated product was 95.8% solvent by weight with a standard deviation of 1.0%. The samples were sieved over a 60 mesh screen and 1.1 grams of the sieved sample was combined with 30.189 grams of clean soil. At 95.8% loading, the BTEX (gasoline components) in the sample would be approximately 38.7 mg/gram soil.

Six one gram samples of the simulated BTEX soil was placed in a 100 ml. volumetric flask. The samples were then diluted with 10.0 ml methanol and allowed to stand for 30 minutes. The samples were then diluted to volume with acetone. The solvent was then analyzed by gas chromatography for toluene, ethyl benzene and p-xylene. The replicate analysis of these samples indicated the concentration of toluene was 25860 $\mu g/gram$ (Std Dev=1900), ethyl benzene 34050 $\mu g/gram$ (Std. Dev.=2930) and p-xylene 34320 $\mu g/gram$ (Std. Dev.=2760). The overall variability at one standard deviation was 7.3% for toluene and 8.0% for ethyl benzene and p-xylene. This singular analysis indicated the total variability of the concentration of the toluene, ethyl benzene and p-xylene was less than the estimated overall variability of the analytical method to be used for the sample analysis. The precision of the analytes in the encapsulated product must be high in order to provide a degree of accuracy in creating the final performance evaluation material—the soil.

In a second sample trial, 'gasoline' was encapsulated to simulate a gasoline in a soil matrix. Analysis of the initial samples indicated the percent loading to be 73.2% with a standard deviation of 6.2. Gas chromatographic analysis of the samples was performed by taking three ~2 gram samples in triplicate and dissolving it in 50.0 ml of methanol. Analytical results indicated toluene concentration 3274 $\mu g/gram$ (std. dev.=248, %RSD=7.6), ethyl benzene 4347 $\mu g/g$ (std. dev.=296, %RSD=6.8) and p-xylene 14922 $\mu g/g$. (std. dev. 931, %RSD=6.2).

Three samples of the pilot encapsulated gasoline in soil (from above) were sent to a typical environmental laboratory for analysis. Each of the three samples was analyzed in triplicate and the data returned for evaluation. The average concentration, standard deviation and percent relative standard deviation (%RSD) for each of the analytes are indicated in the table below.

| Analyte | Average Conc ($\mu g/g$) | Standard Deviation | % RSD |
|---|---|---|---|
| Benzene | 402.1 | 20.5 | 5.1 |
| Toluene | 131.9 | 4.7 | 3.6 |
| Ethyl benzene | 193.8 | 10.9 | 5.6 |
| o-Xylene | 292.1 | 22.5 | 7.7 |
| m- & p-Xylene | 823.8 | 36.3 | 4.4 |

The data returned by the environmental analytical laboratory confirmed that the samples were homogeneous and confirmed findings by the inventor's analysis. With %RSD values near 5%, these samples, when analyzed by numerous laboratories, should display typical performance evaluation data scatter that can be used to demonstrate analytical methodology errors.

Other analytical laboratories are currently analyzing this same pilot gasoline in soil sample detailed above. This round robin is intended to discover any of the sample's weaknesses by other analytical techniques and evaluate the laboratories' analytical methodologies. A second pilot sample is also being prepared in which the concentration of the analytes of interest will be significantly lower—near 1 ppm (part per million—$\mu g/g$).

The foregoing description of a preferred embodiment of the invention has been presented for purposes of illustration and description. It is not intended to be exhaustive or to limit the invention to the precise form disclosed. For example, in addition to the specific encapsulation examples provided above, the iso-octane carrier solvent can be spiked with other analytes such as acetone, benzene, carbon tetrachloride, chloroform, ethyl benzene, methylene chloride, trichloroethane, tetrachloroethylene, xylene, toluene. The embodiment described herein explains the principles of the invention so that others skilled in the art may practice the invention in various embodiments and with various modifications as suited to the particular use contemplated. It is intended that the scope of the invention be defined by the claims appended hereto.

The embodiments of this invention in which an exclusive property or privilege is claimed are defined as follows:

1. A method of preparing performance evaluation soil samples comprising the steps of;

preparing target analytes for encapsulation;

encapsulating said analytes; and placing said encapsulated analytes into a soil matrix to achieve a predetermined analyte concentration in the soil.

2. The method of claim 1, wherein said step of encapsulation includes coacervation and interfacial polymerization.

3. The method of claim 1, wherein the target analytes include oils and greases, nutrients, inorganic metals, organic compounds, cations and anions, and radiochemical compounds.

4. The method of claim 1, wherein said step of preparing target analytes include mixing the analytes in predetermined solvents at desired concentrations.

5. The method of claim 4, wherein said solvents include iso-octane.

6. The method of claim 1, including the step of recovering the encapsulated analytes by filtering and washing.

7. The method of claim 1, including the step of drying the encapsulated analytes.

8. The method of claim 1, including the step of quantitating the encapsulated analytes to determine analyte concentration.

9. The method of claim 1, wherein said soil matrix is dried and sieved to a uniform mesh size.

10. A method of preparing performance evaluation soil samples comprising the steps of;

mixing target analytes in a solvent at predetermined concentrations;

encapsulating the analytes to form microcapsules;

recovering and drying the microcapsules; and introducing the microcapsules into a soil matrix.

11. The method of claim 10, wherein said step of encapsulating the analytes to form microcapsules includes emulsifying the mixture in a solution of polymeric film forming material and polymerizing the emulsified mixture.

12. The method of claim 10, including the step of quantitating the microcapsules after they are recovered and dried.

13. The method of claim 10, wherein said step of encapsulation includes coacervation and interfacial polymerization.

* * * * *